(12) United States Patent
Hitschmann et al.

(10) Patent No.: US 11,324,640 B2
(45) Date of Patent: May 10, 2022

(54) COMPRESSION SLEEVE

(71) Applicant: 3M INNOVATIVE PROPERTIES COMPANY, Saint Paul, MN (US)

(72) Inventors: Guido Hitschmann, Neuss (DE);
Joseph D. Rule, Woodbury, MN (US);
John J. Rogers, Saint Paul, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 408 days.

(21) Appl. No.: 16/461,063

(22) PCT Filed: Nov. 16, 2017

(86) PCT No.: PCT/US2017/061906
§ 371 (c)(1),
(2) Date: May 15, 2019

(87) PCT Pub. No.: WO2018/093977
PCT Pub. Date: May 24, 2018

(65) Prior Publication Data
US 2020/0054493 A1   Feb. 20, 2020

(30) Foreign Application Priority Data
Nov. 21, 2016   (EP) .................................... 16199777

(51) Int. Cl.
*A61F 13/08* (2006.01)
(52) U.S. Cl.
CPC ............ *A61F 13/085* (2013.01); *A61F 13/08* (2013.01)
(58) Field of Classification Search
CPC .... A61F 5/0102; A61F 5/0104; A61F 5/0106; A61F 5/0109; A61F 5/0118; A61F 5/30; A61F 5/32; A61F 2007/0001; A61F 2007/0029; A61F 2007/003; A61F 2007/0031; A61F 2007/0032;
(Continued)

(56) References Cited

U.S. PATENT DOCUMENTS 3,575,782 A * 4/1971 Hansen ............... A61F 13/0273
442/329
4,031,352 A * 6/1977 Oosterberg ........ G05D 23/1909
219/212
(Continued)

FOREIGN PATENT DOCUMENTS

CN   105860019     8/2016
DE   102009007752  12/2012
(Continued)

OTHER PUBLICATIONS

Gerhardts, "Ein neues heizbares Patienten-Wärmkesystem zur Vorbeugung von Unlerkühlungen bei Operationen", Hohenstein Innovationsbörse 2012, 1-19pages.
(Continued)

*Primary Examiner* — Tarla R Patel
(74) *Attorney, Agent, or Firm* — 3M Innovative Properties Company; Trisha D. Adamson

(57) ABSTRACT

Compression sleeve (1) for application circumferentially around a human limb (10) to exert therapeutic pressure on the limb. The compression sleeve has a fabric (80), which comprises viscoelastic strands (90) for providing the fabric with viscoelastic properties.

12 Claims, 3 Drawing Sheets

Figure 1:
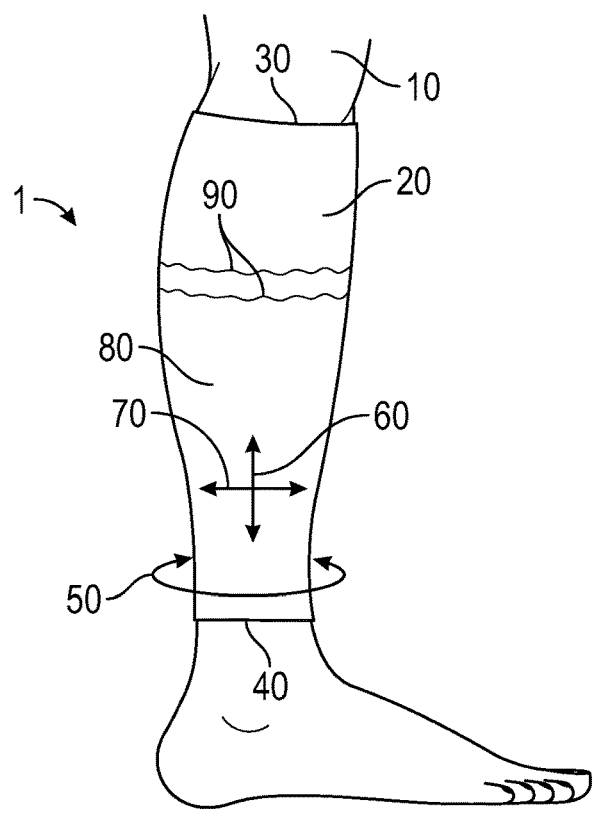

(58) Field of Classification Search
CPC ...... A61F 2007/0034; A61F 2007/0039; A61F 2007/0041; A61F 2007/0042; A61F 2007/0043; A61F 7/02; A61F 7/0233; A61F 7/0234; A61F 7/0236; A61F 13/00034; A61F 13/0038; A61F 2013/00093; A61F 2013/00097; A61F 2013/00192; A61F 2013/00119; A61F 2013/00131; A61F 2013/00148; A61F 2013/00187; A61F 13/08; A61F 13/085; A41D 31/18; A41D 31/185
See application file for complete search history.

(56) References Cited

U.S. PATENT DOCUMENTS

| | | | |
|---|---|---|---|
| 9,610,199 B2* | 4/2017 | Sesi | A61F 13/085 602/201 |
| 2009/0112145 A1 | 4/2009 | Lecomte | |
| 2012/0000251 A1* | 1/2012 | Hu | A61F 13/08 66/171 |
| 2012/0116282 A1 | 5/2012 | Cros et al. | |
| 2013/0131572 A1 | 5/2013 | Cros et al. | |
| 2013/0303957 A1* | 11/2013 | Bauerfeind | A61F 5/0111 602/44 |
| 2016/0076175 A1* | 3/2016 | Rock | A61F 13/08 66/171 |

FOREIGN PATENT DOCUMENTS

| | | |
|---|---|---|
| EP | 2078518 | 7/2009 |
| GB | 2470185 | 7/2015 |
| WO | WO 2009-083254 | 7/2009 |
| WO | WO 2010-007243 | 1/2010 |
| WO | WO 2012-045427 | 4/2012 |
| WO | WO 2014-116497 | 7/2014 |
| WO | WO 2014-184324 | 11/2014 |
| WO | WO 2015/007335 | 1/2015 |
| WO | WO 2015-038598 | 3/2015 |
| WO | WO 2015-094792 | 6/2015 |

OTHER PUBLICATIONS

International Search report for International PCT Application No. PCT/US2017/061906 dated Jan. 26, 2018, 4 pages.
China National Intellectual Property Administration Search Report for Application No. 201780071857.4.

* cited by examiner

COMPRESSION SLEEVE

CROSS REFERENCE TO RELATED APPLICATIONS

This application is a national stage filing under 35 U.S.C. 371 of PCT/US2017/061906, filed Nov. 16, 2017, which claims the benefit of European Application No. 16199777.0, filed Nov. 21, 2016, the disclosure of which is incorporated by reference in its entirety herein.

The present disclosure generally relates to compression devices useful for treatment of edema and other venous and lymphatic disorders of a limb of a patient, in particular to compression sleeves, including compression stockings.

Positive effects of compression therapy on venous lymph return as well as on healing of chronic venous ulcers, e.g. venous leg ulcers, are known. Compression bandages and stockings are the most common compression devices used for compression therapy.

A compression stocking is described, for example, in the European patent application EP 2078518 A2. The stocking has a tubular compressing leg section made of a flexible material, where the section surrounds the leg of a wearer.

The international patent application WO 2014/184324 A1 describes a compression garment for treating lymphedema, comprising a multi-layer sheet arranged for being wrapped around a body part and one or more fasteners for holding the multi-layer sheet in the wrapped configuration. The multi-layer sheet comprises an inelastic layer extending throughout the sheet for maintaining a cross sectional perimeter of the multi-layer sheet substantially constant once wrapped and fastened, and a resilient layer arranged at an inner side of the multi-layer sheet such that, in use, the resilient layer is interposed between the body part and the inelastic layer.

Some compression devices such as bandages or certain devices with adjustable straps can be adjusted—by the patient or a caregiver—in circumference to the size of the patient's limb when put on. For easy application to the limb, these devices do not require elasticity. Once closed, they can be "stiff" and can exert high therapeutic pressure.

On the other hand, sleeve-type compression devices, termed "compression sleeves" herein, are devices that the patient or a caregiver cannot adjust in circumference upon application on the limb, an example being a compression sleeve with a zipper. The zipper permits opening and closing, but no adjusting of the circumference to the size of the limb. Compression sleeves in accordance with the present disclosure include, for example, compression stockings with or without zipper, and leggings with or without zipper, or so-called compression hosiery with or without zipper.

"Limb", in the context of this disclosure, refers to a calf, a thigh, a forearm or an upper arm of a human patient.

Compression sleeves generally need to be quite elastic so that a patient can pull them on before use and pull them off easily after use. Traditional compression sleeves equipped with a zipper also need to be somewhat elastic so that a patient can easily close the zipper, as zippers are hard to close under higher tension. Once put on, i.e. in use, however, less elasticity and a corresponding higher stiffness is desirable, so that the muscle pump is better supported in returning venous blood to the heart when the patient is walking.

The present disclosure attempts to address this requirement. According to this disclosure, it is provided a compression sleeve for application circumferentially around a human limb to exert therapeutic pressure on the limb, the compression sleeve comprising a compression section comprising a fabric, characterized by the fabric comprising viscoelastic strands for providing the fabric with viscoelastic properties.

Viscoelasticity combines elastic and viscous behaviour of materials. Materials having viscoelastic properties provide higher resistance against rapid deformation, i.e. deformation at high strain rates, and lower resistance against slow deformation, i.e. deformation at low strain rates. In a compression sleeve applied around a lower leg, higher strain rates may occur, for example, when the patient is walking or running or in case of foot dorsiflexion. Lower strain rates may occur, for example, as a result of the patient standing, sitting (e.g., if the medical article is wrapped around a knee that is bent in the sitting position), or upon deswelling or decreasing edema.

The viscous properties of the viscoelastic fabric generally provide for increasing resistance to elongation when the fabric is stretched at increasing speeds. The elastic properties of the viscoelastic fabric generally provide for its ability to immediately strive to recover its original length after being elongated. The overall effect is that the viscoelastic fabric can be stretched like other elastomers, but the force required to stretch the fabric depends on both how fast the viscoelastic fabric is being stretched and how far it has been stretched. This is different from elastic materials used in conventional compression sleeves in which the force required to stretch the elastic material varies with how far the elastic material is stretched, but does essentially not vary with how fast the material is stretched.

Many elastic materials exhibit a small degree of viscoelasticity. Viscoelastic strands, in the context of the present disclosure, are strands that have a sufficiently high degree of viscoelasticity to result in a noticeable viscoelastic macroscopic behaviour of a compression device in typical health care applications. Non-viscoelastic strands, on the other hand, have a sufficiently low degree of viscoelasticity, so that the macroscopic behaviour of a compression device in typical health care applications is not a noticeable viscoelastic behaviour.

A strand, in the context of this disclosure, comprises a plurality of fibres or consists of a single fibre. A viscoelastic strand thus comprises one or more viscoelastic fibres. A "fabric comprising viscoelastic strands for providing the fabric with viscoelastic properties" is also referred to herein as the "viscoelastic fabric". Elongation as used herein refers to relative elongation, unless otherwise indicated, and is expressed in percentages. An elongation or deformation value of 140%, for example, thus refers to an increase in length of a material or a strand by 40% over its length after full relaxation and before deformation or expansion, so that, for example, an element of an unexpanded length of 10 units has a length of 14 units when expanded to an elongation of 140%.

When a compression sleeve according to this disclosure is applied to the limb, it may be slowly expanded before application, and it presents little resistance against that slow deformation. It will remain in an expanded state for some time, during which time it can be arranged around the limb. Depending on how its elastic properties are adjusted vs. its viscous properties, the sleeve will return more or less slowly into a less expanded or unexpanded state in which it compresses the limb. Once in use, rapid deformation is caused, for example, by muscle movement when the patient is walking, or by dorsiflexing the foot, when the patient is sitting. The sleeve provides greater resistance against this rapid deformation and thereby provides high short-term stiffness and high therapeutic pressure when the compression sleeve is in use.

A compression sleeve according to the present disclosure has a unique performance due to the viscoelastic strands comprised in the fabric. The viscous nature of a strand particularly refers to its increasing resistance to elongation when it is stretched at high strain rates, i.e. at high speed. The overall effect is that the force required to stretch the fabric depends on both how fast the fabric is being stretched and how far it is stretched.

The inventors of the present disclosure recognized that, in a compression therapy application, muscle contractions (amplitudes) that enable the muscle pump mechanism happen relatively rapidly, causing relatively high strain rates in a compression sleeve employed. The inventors further recognized that, in contrast, conformability to a limb, potential sloughing of the compression sleeve, swelling or deswelling of edema happen relatively slowly, causing relatively low strain rates in the compression sleeve employed. As a result, the inventors found that compression sleeves that employ a fabric comprising viscoelastic strands in accordance with the present disclosure can exhibit a desirable, stiffer behaviour in response to higher strain rates, while exhibiting a desirable, more compliant behaviour in response to lower strain rates.

A dynamic mechanical analysis (DMA) is a method for studying the viscoelastic behaviour of materials. DMA measures viscoelastic moduli like a storage modulus E' and a loss modulus E". E' and E" together form a complex modulus, their ratio E"/E' being a property of materials as they are deformed under a periodic sinusoidal deformation (stress or strain). The viscoelastic strands of the fabric exhibit, for a sinusoidal deformation of the strand in a stretch direction in a dynamic mechanical analysis, a phase lag δ between strain and stress, a storage modulus E' and a loss modulus E" (explained in more detail below) where tan δ=E"/E'. Typical sinusoidal deformations, usable for determining E' and E" of strands suitable for sleeves according to the present disclosure, have frequencies in the range of about 1 Hz to 10 Hz with deformation amplitudes of about 50 μm to about 100 μm on strands of about 17-19 mm length.

The viscoelastic behaviour of strands useful in a sleeve according to the present disclosure can be characterized by performing a DMA on a Q800 dynamic mechanical analyzer, available from TA Instruments, New Castle, Del., U.S.A., in tensile mode. A strand, e.g. a strand with an effective cross-sectional area of 0.1 mm², can be mounted in the tensile grips with a relaxed test length between 17 mm and 19 mm. The temperature is raised continuously, starting from −25° C., at a rate of 3° C. per minute, up to 150° C. At each temperature, the sample is analyzed by exposing it to elongations with amplitudes of 75 microns at a frequency of 1 Hz. The force is determined continuously, and E' and E" are derived from the force and from the phase lag δ between the elongation curve and the force curve for that temperature. At an amplitude of 75 μm and a frequency of 1 Hz, the highest strain rate is about 0.47 mm/s.

At a given strain rate, both E' and E" are functions of temperature. The ratio E"/E'=tan δ is therefore also a function of temperature. tan δ is a measure for the amount of viscous properties in relation to the elastic properties. A graph of tan δ over temperature typically exhibits a peak in the transition regime between glassy and rubbery state of the strand material, the peak maximum being at a particular temperature. The temperature at which the peak maximum is located, is considered to be the glass transition temperature of the strand material. In order to facilitate application of a sleeve according to the present disclosure to the limb of a patient, it is preferred that the glass transition temperature of the viscoelastic strand material is in the range of temperatures at which the sleeve is used by a patient or caregiver, e.g. in ranges comprising the body temperature of about 37° C. and room temperature of about 21° C. A preferred range for the glass transition temperature is from about 15° C. to about 55° C.

For viscoelastic strands in a sleeve according to the present disclosure, it is desirable that tan δ is greater than 0.3 at the glass transition temperature, because this balance between elastic and viscous properties results in noticeable viscoelastic behaviour of the sleeve, which in turn facilitates high resistance against rapid deformation and lower resistance against slow deformation of the sleeve. Values for tan δ of between 0.2 and 0.4, as measured in a dynamic mechanical analysis at an elongation of 75 μm at an elongation frequency of 1 Hz and with a strand heat rate (heat-up rate) of 3° C./minute, may still result in an acceptable viscoelastic behaviour of the fabric.

Stress, in this context, is the force resulting in deformation in a stretch direction. Strain is the linear amount of deformation, i.e. elongation, in the stretch direction, measured for example in millimetres. The strain rate is the speed of the deformation, measured, for example, in millimetres per second.

For example, a sinusoidal stress may be applied to the fabric and the strain in the fabric may be measured. For perfectly elastic strands, the resulting strain and the applied stress would be in phase. For a hypothetical purely viscous strand, there would be a 90 degree phase lag of strain with respect to stress. Viscoelastic materials have characteristics between these two extremes, so that some phase lag will occur during DMA tests of the fabric. The storage modulus E' relates to the stored energy and represents the elastic portion. The loss modulus E" relates to the energy dissipated as heat, representing the viscous portion. The requirement E"/E'>0.3 thus means that the strand—and thus the fabric—is required to have viscous properties above a certain lower limit in the temperature range of application of the sleeve to the limb, e.g. at room temperature or at body temperature.

The peak maximum of tan δ, drawn over temperature, may thus define the glass transition temperature of the viscoelastic strand material of the fabric. The glass transition temperature may have values between 15° C. and 55° C. The compression sleeve may thus be particularly well applied at room temperature and/or at body temperature.

The extent of compression provided by a compression sleeve according to the present disclosure can be related to, inter alia, the size and cross section of the viscoelastic strands and/or the number and/or the density of parallel viscoelastic strands employed, whereby increased compression can generally result from using a greater number of thicker viscoelastic strands in the compression sleeve. Suitably, the number of parallel viscoelastic strands per inch of width (conventionally referred to as "epi", 1 inch=2.54 cm) may range from about 4 to about 100 epi, preferably from about 10 to about 50 epi, more preferably from about 10 to about 25 epi (corresponding to from about 1.6 to about 39.4 strands per cm, preferably from about 3.9 to about 19.7 strands per cm, more preferably from about 3.9 to about 9.8 strands per cm). The density of parallel viscoelastic strands may be between 1.5 and 40.0 strands per cm of width.

The linear mass density of the viscoelastic strands used in a compression sleeve according to the present disclosure may range, for example, from about 0.5 mg/m to about 600 mg/m (5-6000 dtex, where 1 dtex is a strand linear mass density of 1 g per 10000 m of strand length). It is preferred to have strands of a linear mass density of about 5 mg/m to about 100 mg/m (50-1000 dtex). The inventors of the compression sleeve currently consider a linear mass density range for the strands of about 10 mg/m to about 60 mg/m (100-600 dtex) to be the most preferred range.

Linear mass density measurements on a viscoelastic strand should be run at room temperature by first elongating the strand to an elongation of 130%, then letting it relax over 48 hours. For straightening the strand, a force of 0.5 cN per tex (where 1 tex=10 dtex) is applied. After straightening for 10 seconds, the strand is cut to length for weighing and determining its linear mass density.

In some embodiments, the linear mass density of the viscoelastic strands is 600 mg/m or less.

For use in compression sleeves of the present disclosure, particularly for treatment and/or management of venous leg ulceration, it is believed that a strand density of from about 10 to about 25 epi (3.9 strands per cm to about 9.8 strands per cm) together with a strand linear mass density of about 5500 dtex (550 mg/m) or less, more favourably about 3000 dtex (300 mg/m) or less, most favourably about 2500 dtex (250 mg/m) or less can be beneficial in providing desirable ease in handling of the compression sleeve itself as well as desired therapeutic compressive force without providing undesirably high resting pressures.

A viscoelastic strand recovers after it is deformed by elongation from its fully relaxed state. The fully relaxed state can be reached by heating the viscoelastic strand to a temperature of at least 40° C. in the absence of constraint or applied force for 48 hours. After the viscoelastic strand is strained to 150% elongation, it can be characterized by recovering at least 70% of its elongation beyond 100% after 48 hours at room temperature. In other words, after recovering 70% of its original 50% elongation beyond 100%, the overall elongation of the viscoelastic strand would be 115% elongation. In some embodiments, the viscoelastic strand can recover at least 75% of its deformation; in some embodiments, at least 80% of its deformation; in some embodiments, at least 90% of its deformation; in some embodiments, at least 95% of its deformation; and in some embodiments, 100% of its deformation, with room temperature being generally about 21° C.

In some embodiments, a viscoelastic strand can be further characterized by recovering at least 20% of its deformation beyond 100% after 30 minutes at room temperature after being strained to 150% elongation; in some embodiments, at least 30% of its deformation beyond its 100% elongation; in some embodiments, at least 40% of its deformation beyond its 100% elongation; in some embodiments, at least 50% of its deformation beyond its 100% elongation; and in some embodiments, at least 60% of its deformation beyond the 100% elongation.

Tensile stiffness of a fabric, in the context of the present disclosure, is the ratio of F/d, where F is a force applied on the fabric in a specific direction, and d is the displacement by elongation in this direction caused by this force, in analogy to Hooke's law. In some embodiments, the viscoelastic fabric can be further characterized by having, at room temperature, a first tensile stiffness V1 at a first (i.e., higher) strain rate S1 and a second tensile stiffness V2 at a second (i.e., lower) strain rate S2, wherein the ratio of S1/S2 is at least 100 (in some embodiments, at least 150, and in some embodiments, at least 200), and wherein the ratio of V1/V2 is at least 1.5. In some embodiments, the ratio of V1/V2 can be at least 2; in some embodiments, at least 2.5; in some embodiments, at least 3; in some embodiments, at least 3.5; in some embodiments, at least 4; in some embodiments, at least 4.5; and in some embodiments, at least 5. In some embodiments, the ratio of V1/V2 can be no greater than 10; in some embodiments, no greater than 9; in some embodiments, no greater than 8; in some embodiments, no greater than 7; and in some embodiments, no greater than 6. As a result, the viscoelastic fabric can be characterized by recovering at least 70% of its deformation beyond 100% elongation after 48 hours at room temperature after being strained to at least 125% elongation, and in some embodiments, at least 50% of its deformation beyond 100% elongation; in some embodiments, at least 75% of its deformation beyond 100% elongation; in some embodiments, at least 80% of its deformation beyond 100% elongation; in some embodiments, at least 90% of its deformation beyond 100% elongation; in some embodiments, at least 95% of its deformation beyond 100% elongation; in some embodiments, at least 97% of its deformation beyond 100% elongation; in some embodiments, at least 98% of its deformation beyond 100% elongation; and in some embodiments, at least 99% of its deformation beyond 100% elongation.

In some embodiments, the viscoelastic fabric can be further characterized by recovering at least 20% of its deformation beyond 100% after 30 minutes at room temperature after being strained to 150% elongation; in some embodiments, at least 30% of its deformation beyond 100%; in some embodiments, at least 40% of its deformation beyond 100%; in some embodiments, at least 50% of its deformation beyond 100%; and in some embodiments, at least 60% of its deformation beyond 100%.

In some embodiments, the viscoelastic fabric can be further characterized by having, at room temperature, a first tensile stiffness T1 at a first (i.e., higher) strain rate S1 and a second tensile stiffness T2 at a second (i.e., lower) strain rate S2, wherein the ratio of S1/S2 is at least 100 (in some embodiments, at least 150, and in some embodiments, at least 200), and wherein the ratio of T1/T2 is at least 1.5. In some embodiments, the ratio of T1/T2 can be at least 2; in some embodiments, at least 2.5; in some embodiments, at least 3; in some embodiments, at least 3.5; in some embodiments, at least 4; in some embodiments, at least 4.5; and in some embodiments, at least 5. In some embodiments, the first strain rate S1 can be no greater than about 500 cm/min; in some embodiments, no greater than 100 cm/min, and in some embodiments, no greater than 50 cm/min. In some embodiments, the second strain rate S2 can be at least about 0.01 cm/min; in some embodiments, at least 0.1 cm/min, and in some embodiments, at least 0.5 cm/min.

When a sleeve according to the present disclosure is applied on the limb, the extension of the limb defines the following directions: The circumference of the limb defines circumferential directions of the sleeve. The long extension of the limb defines axial directions of the sleeve. Radial directions of the sleeve are directions orthogonal to the axial directions.

In one aspect of the disclosure, the compression sleeve may be elongate, i.e. it has an elongated shape and extends lengthwise in axial directions. An elongate sleeve may comprise a plurality of axial sections.

The sleeve, elongate or not, may comprise a thigh section for application around the thigh, and/or a calf section for application around at least a portion of the calf, and/or a foot section for application around at least a portion of the foot. The foot section, in turn, may comprise a heel section for application around at least a portion of the heel, an optional middle section for application around at least a portion of the metatarsus, and an optional toe section for application around at least a portion of the toes. In certain embodiments, the compression sleeve comprises a thigh section only or a calf section only. In certain other embodiments, the compression sleeve comprises a calf section and a foot section.

In one aspect of the present disclosure, the compression sleeve may be a compression stocking. In the present disclosure, a stocking is considered to be a sleeve further comprising a foot section. The foot section comprises at least a heel section, and may further comprise a middle section and/or an optional toe section.

In order to support the muscle pump, therapeutic compression for the leg is normally required for the calf section, but to a lesser degree for the thigh section or the foot section. However, each of the sections a compression sleeve according to the present disclosure may have (i.e. a thigh section, a calf section, a heel section, a middle section or a toe section) may be adapted to provide therapeutic compression. Other sections may be adapted to provide other functions, but no compression. An axial section of the sleeve that is adapted to provide therapeutic compression to the limb is referred to as a "compression section" herein.

A sleeve according to the present disclosure provides therapeutic compression by having viscoelastic properties. These properties result from the properties of the materials of which the sleeve is made. The compression sleeve comprises a fabric which comprises viscoelastic strands. When the viscoelastic strands of the fabric are expanded lengthwise, they strive to return to their original length, thereby contracting the fabric. The fabric may extend circumferentially around the limb, when the sleeve is in use. It may extend around the limb either for a full 360° circumference or for a part of the circumference of the limb. Where the fabric extends circumferentially around the limb, its contraction causes the fabric to exert a radial pressure on the skin of the limb.

In an aspect of this disclosure, the viscoelastic strands exhibit viscoelastic properties in a temperature range comprising typical room temperatures and the human body temperature. Such a temperature range is the range between 15° C. and 55° C. Viscoelasticity of the strands in other temperature ranges is less relevant to the performance of the sleeve. Viscoelasticity expresses itself by a phase lag δ between elongation and force in a dynamic mechanical analysis run at an elongation frequency of 1 Hz and an elongation amplitude of 75 µm and at a specific heat rate of the strand, e.g. 3° C. per minute. A graph showing tan δ as a function of temperature exhibits a peak maximum at a certain temperature in the transition regime between glassy and rubbery state, which temperature is considered the "glass transition temperature" of the strand material. Since glass transition is a kinetic phenomenon, the glass transition temperature varies with heat rate of the strand. The glass transition temperature corresponds to the temperature where the strands exhibit viscoelastic behaviour.

In certain embodiments of the present disclosure, the glass transition temperature of the viscoelastic strands is between 15° C. and 55° C., as determined by the position of the peak maximum of a graph of tan δ over temperature, where δ is the phase lag between elongation curve and force curve in a dynamic mechanical analysis run at an elongation frequency of 1 Hz, an elongation amplitude of 75 µm and at a heat rate of 3° C./minute.

Strands having such glass transition temperatures provide for a fabric having viscoelastic properties in the relevant temperature range, in which the application of the sleeve to the patient's limb is typically done.

In one aspect, the fabric may be thin and flat before use, and the viscoelastic fibers extend in the plane of the fabric, or, in other words, they extend parallel to the major surfaces of the fabric. In one embodiment, more than 50% of the viscoelastic fibers of the fabric are arranged in the compression sleeve such that the fibers extend lengthwise in a circumferential direction, when the compression sleeve is in use. Lengthwise extension of a strand refers to extension in the long direction of the strand. This arrangement increases the compression force originating from the fibers. In other embodiments, the fibers extend lengthwise in a direction that forms an angle of between 5° and 90° with the circumferential direction. In one specific embodiment, the viscoelastic fibers in the fabric, and the fabric itself, are arranged in the compression sleeve such that the fibers extend lengthwise in a direction forming an angle of 45° with the circumferential direction, when the compression sleeve is applied on the limb. The latter arrangements may provide for some viscoelastic properties of the compression sleeve in axial directions, which may be beneficial in certain scenarios.

In certain embodiments the viscoelastic strands extend parallel to each other. They may extend parallel to each other in a circumferential direction of the sleeve, when the sleeve is in use, i.e. when it is applied to the limb in order to provide compression. In certain embodiments at least 50% of the viscoelastic strands extend parallel to each other in a circumferential direction.

Generally, viscoelastic strands provide viscoelastic properties in their long direction. Orientation of the viscoelastic strands in the fabric determines the direction, or the directions, in which the fabric is provided with viscoelastic properties. Since a compression sleeve is generally supposed to exert radial pressure on the limb (in a direction generally perpendicular to the skin and towards the bone), a sleeve according to this disclosure, and in particular the compression section, has viscoelastic properties in one or more directions orthogonal to a surface normal of the fabric, when the compression sleeve is in use. In certain embodiments, the strands provide viscoelastic properties to the fabric in a circumferential direction, when the sleeve is in use. In certain embodiments, the strands provide viscoelastic properties to the fabric in axial directions, when the sleeve is in use. Therefore, in one aspect of the disclosure, the viscoelastic strands may be arranged such as to provide the fabric with viscoelastic properties in a circumferential direction, when the sleeve is in use. In certain embodiments, the viscoelastic strands may be arranged such as to provide the fabric with viscoelastic properties in a circumferential direction and in an axial direction, when the sleeve is in use.

Viscoelastic strands for a compression sleeve in accordance with the present disclosure may be, for example, polyurethane strands, polyurea strands, polyether strands, polyester strands, poly(meth)acrylate strands, polyolefin strands, or polyvinyl chloride strands. The viscoelastic strands may comprise polyurethane, polyurea, polyether, polyester, poly(meth)acrylate, polyolefin, or polyvinyl chloride. Any percentage of polyurethane strands, polyurea strands, polyether strands, polyester strands, poly(meth)acrylate strands, polyolefin strands, and polyvinyl chloride strands may be mixed to form the viscoelastic strands comprised in the fabric. In a specific embodiment, the fabric comprises viscoelastic polyurethane strands. In another specific embodiment, the fabric comprises one or more strands comprising a plurality of polyurethane fibres. These fibres may be twisted or stranded to form the strand. Alternatively, they may be arranged parallel to each other in the strand.

Whether its fibres are twisted or parallel, the strand may comprise a sheath enveloping the fibres comprised in it.

In certain other embodiments, the fabric comprises, or is made of, strands comprising a viscoelastic core fibre and a thin sheath around the core fibre. In some of these embodiments, the linear mass density of the sheath is between 3% and 10% of the linear mass density of the strand. In some of these embodiments, the core fibre consists of polyurethane. In some of these embodiments, the sheath consists of polypropylene.

In certain other embodiments, the fabric comprises a mixture of polyurethane strands and polyurea strands, polyether strands, polyester strands, poly(meth)acrylate strands, polyolefin strands, or polyvinyl chloride strands.

In order to facilitate application and removal of a compression sleeve according to the present disclosure, it is desirable that the compression sleeve and the fabric have viscoelastic properties in a temperature range which encompasses typical room temperature and human body temperature. Therefore, in one aspect of this disclosure, the viscoelastic strands are adapted for providing the fabric with viscoelastic properties at temperatures of between 15° C. and 55° C. These temperatures refer to temperatures of the fabric.

In one aspect of the present disclosure, the compression sleeve further comprises non-viscoelastic strands. For example, the fabric may comprise non-viscoelastic strands. Such strands may be useful in providing certain desired mechanical properties to the compression sleeve or to the fabric. In certain embodiments, for example, the sleeve comprises essentially purely elastic, non-viscoelastic strands. Such strands may help provide greater resistance against slow deformations of the sleeve, e.g. when the patient stands for a longer time.

For good performance of the sleeve, a suitable balance between viscous properties and elastic properties of the fabric is required. This can be achieved, amongst other factors, by selecting the kind and/or amount of viscoelastic strands, or the ratio of density of viscoelastic strands to density of non-viscoelastic strands. These selections can be made for the entire fabric, or only for portions of the fabric. Portions of the fabric may comprise only elastic, non-viscoelastic strands and be free of viscoelastic strands. Portions of the fabric may be free of elastic, non-viscoelastic strands. A too high elastic modulus of the strands, i.e. a too high tensile stiffness of the fabric, may result in a high supine pressure on the limb, which may make it difficult to put the sleeve over the limb. On the other hand, a purely or predominantly viscous behaviour may result in the sleeve losing too much of its tension when the patient does not move for a longer time. To prevent this, the viscoelastic strands should exhibit a suitable balance between elastic and viscous properties. Alternatively, the fabric could comprise a suitable amount of elastic, non-viscoelastic strands in addition to the viscoelastic strands. A good balance is achieved if the therapeutic pressure on the limb remains above a level of about 5 mm Hg, preferably between about 15 and about 40 mm Hg, after an extended period (e.g. five minutes) of no movement of the patient, while the compression sleeve can still be put on easily by the patient.

In other embodiments, the sleeve comprises rigid strands. For example, the fabric may comprise rigid strands. Rigid strands are strands that cannot be elongated, e.g. in axial directions. Rigid strands may help stabilize the sleeve. Suitably arranged in circumferential directions, rigid strands may provide an "abutment" against excessive circumferential elongation of the sleeve: They may be arranged such that under no tension or under normal circumferential tension these strands are curved and provide no resistance to small further expansion, but become fully stretched when the sleeve is close to overstretching. In their fully stretched state they may prevent any further circumferential expansion of the sleeve.

In the context of the present disclosure, two strands are referred to as being adjacent or adjacent to each other if they are arranged next to each other and no third strand is arranged between them.

In the context of the present disclosure, two or more strands are referred to as being parallel or parallel to each other if their distance is constant over a considerable length of the strands. Curved strands can be parallel to each other.

In one aspect, in a compression sleeve comprising viscoelastic strands and non-viscoelastic strands, such strands may be arranged parallel to each other in an alternating manner. Thus, in certain embodiments, two viscoelastic strands and one non-viscoelastic strand are arranged parallel to each other and such that the one non-viscoelastic strand is arranged between the two viscoelastic strands, and adjacent to each of the viscoelastic strands. Such arrangements may provide for a desired combination of mechanical properties of the compression sleeve, which is uniformly distributed over the surface of the sleeve.

In one aspect of the present disclosure, the fabric of the compression section may be a knitted, woven or non-woven fabric. A knitted or woven fabric may be knitted or woven from a plurality of strands, some or all of which strands are viscoelastic strands. A non-woven fabric may be formed from a plurality of strands, some or all of which strands are viscoelastic strands.

The compression section of the sleeve may be arranged in different locations in the sleeve. In one aspect, the compression section may be arranged such as to exert therapeutic pressure on the calf, when the compression sleeve is in use. In a specific embodiment, the compression sleeve is a compression stocking, or is comprised in a compression stocking, and the compression section is arranged to exert therapeutic pressure on the calf, when the compression stocking is in use. In other embodiments, the compression sleeve is a compression stocking, or is comprised in a compression stocking, and the compression section is arranged to exert therapeutic pressure on the thigh, or on both the calf and the thigh, when the compression stocking is in use.

Applying a compression sleeve on a patient's limb is sometimes referred to as "donning", removal is sometimes referred to as "doffing". Certain traditional compression sleeves are hard to don, because they must provide a considerable elastic force in order to compress the limb effectively after application. Before donning, the patient or a caregiver may have to open the sleeve wide enough, against the elastic force, for the limb to slip in. Similarly, when removing a traditional sleeve, it may have to be opened to some degree, against the elastic force, in order to reduce friction between the skin and the sleeve and to be able to remove the sleeve from the limb. Sleeves equipped with a zipper are generally easier to remove, because they do not need to be widened before removal. It is, however, difficult to put them on, because it is usually difficult to close a zipper under high tension.

A sleeve according to the present disclosure is generally easier to don, because its fabric comprises viscoelastic strands so that, after opening and widening, it keeps the wider shape for a certain time before it has reached its original shape. It can be applied on the limb during this time almost without tension. If the sleeve comprises a zipper, the zipper may be closed during this time with less or even without tension.

Hence, in one aspect of the disclosure, the compression sleeve may comprise a zipper for facilitating removal from the limb, or application to the limb, or both. In certain embodiments, the zipper is attached to the fabric. It may, for example, be arranged between two circumferentially adjacent portions of the fabric. In certain embodiments, the zipper is attached to the compression section. It may be attached to the compression section outside the fabric or inside the fabric or both. In certain embodiments, the zipper is operable to separate two portions of the compression section. In certain of these embodiments, the zipper is operable to separate two portions of the fabric. In some embodiments, the zipper extends in an axial direction, when the sleeve is in use. Generally, the zipper may be attached to the compression zone or to the fabric by sewing or welding or by an adhesive.

In a specific embodiment according to the present disclosure, the compression sleeve comprises a calf section and a foot section, wherein the compression section comprises at least a portion of the calf section. The sleeve further comprises a zipper extending axially when the sleeve is in use. In this embodiment, the viscoelastic strands have a linear mass density of 600 mg/m or less.

In one aspect of the present disclosure, the compression sleeve may comprise a heating thread. In some embodiments, the heating thread may be arranged and adapted to heat one or more of the viscoelastic strands. In some embodiments, a heating thread may be arranged and adapted to heat one or more of elastic, non-viscoelastic strands, that may be present. Generally, at higher temperatures, viscoelastic strands and some elastic, non-viscoelastic strands tend to have a lower elasticity modulus and can thus be elongated with less force. Heating the viscoelastic strands just before and/or during application of the sleeve to the patient's limb may make it easier to put the sleeve on, because the fabric can be expanded with less force. Similarly, heating before and/or during removal of the sleeve may make the removal easier, because less force is required to expand the sleeve.

In some embodiments, the heating thread can be heated electrically. In these embodiments, the heating thread is electrically conductive and can be connected, for example, to a power source, e.g. a battery, that provides electrical current flowing through the heating thread. The heating thread has a suitably chosen ohmic resistance, so that the current heats the heating thread to a suitable temperature. An electric or electronic temperature controller may be used to heat the heating thread to a suitable temperature. Suitable temperatures may be in the range of 50-70° C., for example 60° C. At such temperatures, typical viscoelastic and certain elastic, non-viscoelastic strands soften sufficiently to facilitate easier application and removal of the sleeve. To protect the patient's skin from heat, the compression sleeve may be equipped with a suitable temperature-insulating liner, or the patient might wear a second, temperature-insulating sleeve under the compression sleeve. Heating is only required and desired during application and removal. The battery can thus be removed after applying the sleeve to the limb.

Figure 2:
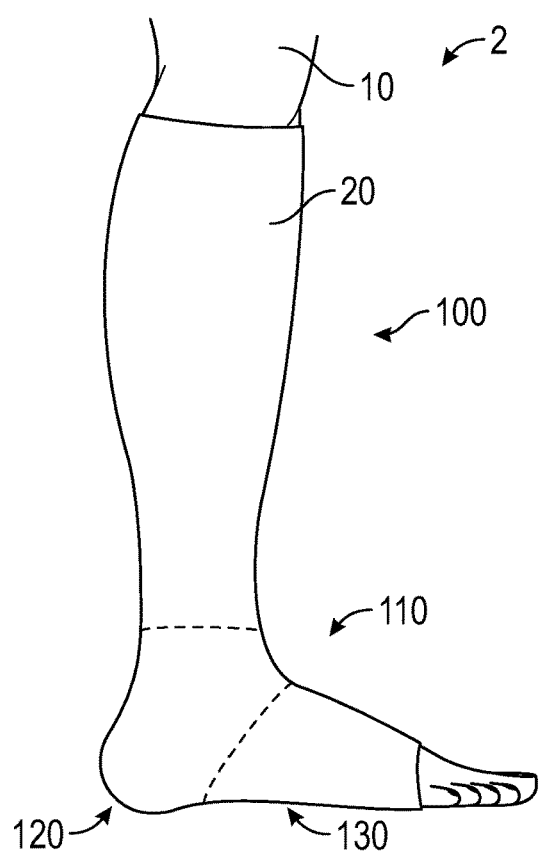
Figure 3:
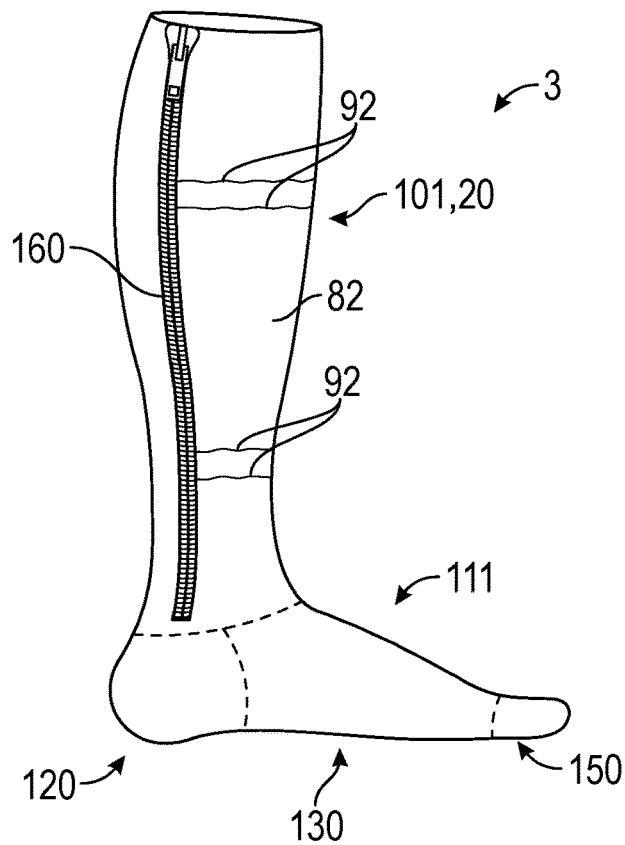
Figure 4:
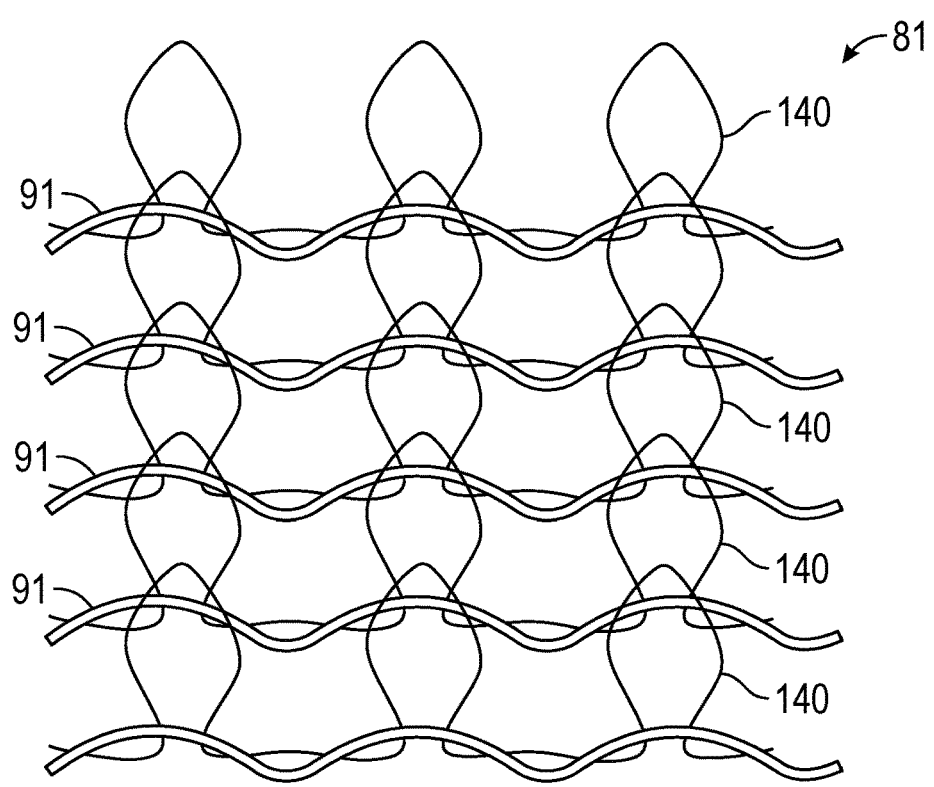

The invention will now be described in more detail with reference to the following Figures exemplifying particular embodiments of the invention:

FIG. 1 Perspective view of a compression sleeve according to the present disclosure, applied on a human lower leg;

FIG. 2 Perspective view of a second compression sleeve according to the disclosure, applied on a human lower leg;

FIG. 3 Perspective view of a third compression sleeve according to the disclosure, comprising a zipper;

FIG. 4 Plan view of a fabric comprising viscoelastic strands; and

Figure 5:
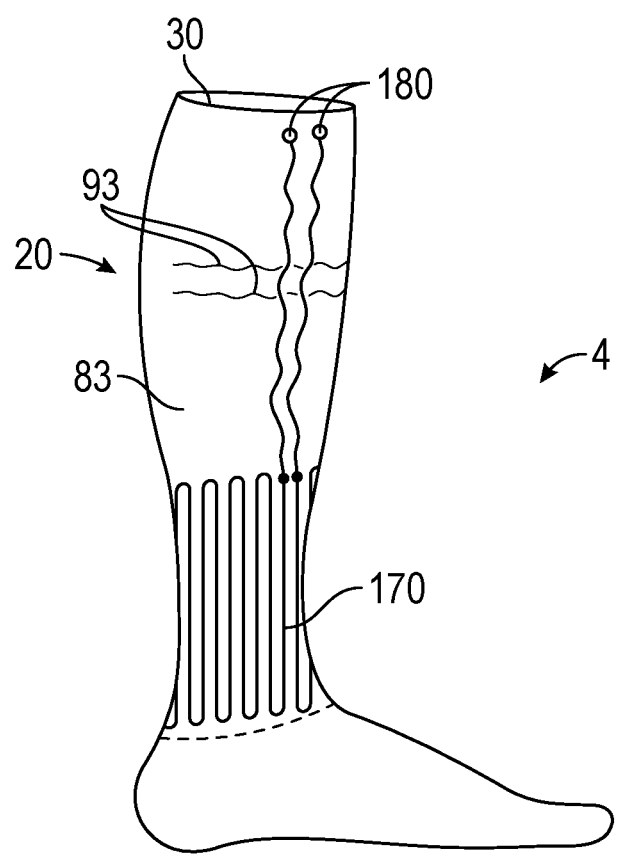

FIG. 5 Perspective view of a fourth compression sleeve according to the disclosure, comprising a heating thread.

In the perspective view of FIG. 1, a first compression sleeve 1 according to the present disclosure is shown applied circumferentially around a human lower leg 10, around the calf. The first compression sleeve 1 applies therapeutic compression on the calf. The sleeve 1 comprises a compression section 20, which extends from the upper edge 30 of the sleeve 1 to its lower edge 40.

The circumference of the calf defines circumferential directions 50 of the sleeve 1. The long extension of the calf defines axial directions 60 of the sleeve 1, these are generally directions along the calf. Radial directions 70 of the sleeve 1 are directions orthogonal to the axial directions 60.

The first compression sleeve 1 comprises a calf section only. The sleeve 1 consists of a knitted fabric 80 which comprises a large number of viscoelastic strands 90, of which only two are shown for reasons of clarity. The viscoelastic strands 90 are elongate, arranged parallel to each other, and they extend in a circumferential direction 50, thereby providing viscoelastic properties to the fabric 80 in this circumferential direction 50.

FIG. 2 is a perspective view of a second compression sleeve 2 according to this disclosure, in use, i.e. applied on a lower leg 10. It is identical to the first sleeve 1 of FIG. 1, except that in addition to the calf section 100 it comprises a foot section 110. The foot section 110 in turn comprises a heel section 120 and a middle section 130. Sections are shown separated by dotted lines in FIG. 2. Of these sections, only the calf section 100 comprises viscoelastic strands 90 (not shown) and is adapted to provide higher therapeutic compression, hence the calf section 100 is a compression section 20 of the second sleeve 2.

A third compression sleeve 3 according to the invention is shown, in perspective view, in FIG. 3. The third sleeve 3 comprises a calf section 101 and a foot section 111. The foot section 111 in turn comprises a heel section 120, a middle section 130 and a toe section 150, so that the sleeve 3 is a compression stocking 3. The foot section 111 of this stocking 3 comprises a conventional elastic, non-viscoelastic material, while the calf section 101 comprises a fabric 82 which in turn comprises viscoelastic strands 92, oriented in circumferential directions 50 when the stocking 3 is in use. For clarity, only four of the many parallel viscoelastic strands 92 are shown. The viscoelastic strands 92 provide the fabric 82 with viscoelastic properties in the length direction of the strands 92. Of the axial sections of the stocking (i.e. calf section 101, heel section 120, middle section 130, and toe section 150), only the calf section 101 is adapted to provide therapeutic compression, hence the calf section 101 is a compression section 20 of the third sleeve 2.

The compression section 20, i.e. the calf section 101, of the stocking 3 comprises a zipper 160. The zipper 160 is arranged within the compression section 20 and extends lengthwise in axial directions 60 of the stocking 3, when the stocking 3 is in use. The zipper 160 facilitates separation of the compression zone 20, so that the stocking 3 can be put on more easily. First, with the zipper 160 open, the patient would slip his foot into the foot section 111. Due to the viscoelastic properties of the fabric 82, the compression section 20 can then be manually expanded or stretched circumferentially before application around the calf and will not immediately, but slowly return to its unexpanded shape. Expansion of the compression section 20 can be done, for example, step by step, starting from the heel section 120 and working upwards. The zipper 160 may then be closed step by step, following the stepwise expansion of the compression section 20.

The integration of a zipper 160 into the stocking 3 can, for example, be done by sewing or by welding or by an adhesive.

The viscoelastic properties of the fabric 82 are chosen such that, after expansion, it takes a few seconds for the compression section 20 to contract and return to its unexpanded shape. During this time, the patient can apply the stocking 3 to his lower leg and close the zipper 160 with less tension or without tension. The compression section 20 continues to contract towards its unexpanded shape, which it attains typically after a minute or several minutes. Once the compression section 20 has taken its original shape, the compression section 20 exerts adequate therapeutic pressure on the calf of the patient.

Since the area of the Achilles tendon sees particular large relative changes in circumference during movement, it may be advantageous to provide the corresponding portion of the compression section 20 with both viscoelastic strands and elastic, non-viscoelastic strands alternately or in parallel to avoid folds or slippage. The compression contribution provided by the elastic, non-viscoelastic strands does not need to be higher than in low-compression class stockings so that donning is still easy.

In an alternative embodiment, the fabric 82 of the compression section 20 of the third sleeve 3 further comprises elastic, but non-viscoelastic strands. In that case, the fabric 82 would also have a certain additional amount of elastic properties, beyond those brought in by the elastic behaviour of the viscoelastic fibers 92. Depending on the number of those elastic, but non-viscoelastic strands, the elastic properties may result in some additional immediately-restoring tension being present after expansion of the compression zone 20. The number and properties of non-viscoelastic strands can be chosen such that the remaining tension is sufficiently low so that the zipper 160 can be closed easily.

FIG. 4 is a sketch of a woven fabric 81 that may be used in a compression sleeve according to the present disclosure. The fabric 81 comprises warp threads 140 and interwoven viscoelastic strands 91 forming the weft threads. The fabric 81 and its viscoelastic strands 91 are arranged in the compression sleeve such that the long direction of the viscoelastic strands 91 is oriented in a circumferential direction 50, when the sleeve is applied on a limb of a patient.

FIG. 5 is a perspective view of a fourth compression sleeve 4 according to the present disclosure. The compression section 20 is the calf section. It comprises a fabric 83 provided with viscoelastic properties by a large number of parallel viscoelastic strands 93 as described above, of which only two are shown. The fourth sleeve 4 comprises an electrically conductive heating thread 170, arranged in the fabric 83 and meandering in the lower portion of the compression section 20. The ends of the heating thread 170 are electrically connected to two electrically conductive press studs 180 arranged at the upper edge 30 of the sleeve 4. A battery can be connected to these press studs 180, so that an electrical current flows through the heating thread 170 and heats the viscoelastic strands 93 in the portion of the fabric 83 through which the heating thread 170 meanders.

What is claimed is:

1. Compression sleeve for application circumferentially around a human limb to exert therapeutic pressure on the limb, the compression sleeve comprising:
   a compression section comprising a fabric;
   wherein the fabric comprises viscoelastic strands for providing the fabric with viscoelastic properties and an elastic, non-viscoelastic strand with elastic properties to provide greater resistance against slow deformation; and
   wherein a glass transition temperature of the viscoelastic strands is between 15° C. and 55° C., as determined by the position of a peak maximum of a graph of tan δ over temperature, where δ is a phase lag between elongation curve and force curve in a dynamic mechanical analysis run at an elongation frequency of 1 Hz, an amplitude of 75 µm and at a heat rate of 3° C./minute;
   wherein two viscoelastic strands and one elastic non-viscoelastic strand are arranged parallel to each other, and such that the one elastic, non-viscoelastic strand is arranged between the two viscoelastic strands and adjacent to each of the two viscoelastic strands.

2. Compression sleeve according to claim 1, wherein the viscoelastic strands are arranged such as to provide the fabric with viscoelastic properties in a circumferential direction when the sleeve is in use.

3. Compression sleeve according to claim 1, wherein the fabric is a knitted or a woven or a non-woven fabric.

4. Compression sleeve according to claim 1, wherein the compression section is arranged such as to exert therapeutic compression on the human limb, when the compression sleeve is in use.

5. Compression sleeve according to claim 1, further comprising a zipper for facilitating removal of the compression sleeve from the limb.

6. Compression sleeve according to claim 5, wherein the zipper is attached by sewing or welding or by an adhesive.

7. Compression sleeve according to claim 1, wherein the viscoelastic strands comprise polyurethane, polyurea, polyether, polyester, poly(meth)acrylate, polyolefin, or polyvinyl chloride.

8. Compression sleeve according to claim 1, wherein the viscoelastic strands are adapted for providing the fabric with viscoelastic properties at temperatures of between 15° C. and 55° C.

9. Compression sleeve according to claim 1, further comprising a heating thread, arranged and adapted to heat one or more of the viscoelastic strands.

10. Compression sleeve according to claim 1, wherein a density of the viscoelastic strands is between 1.5 and 40.0 strands per cm.

11. Compression sleeve according to claim 1, wherein a linear mass density of the viscoelastic strands is 600 mg/m or less.

12. Compression sleeve according to claim 1, comprising a calf section and a foot section, wherein the compression section comprises at least a portion of the calf section, further comprising a zipper extending axially when the sleeve is in use, wherein the viscoelastic strands have a linear mass density of 600 mg/m or less.

* * * * *